(12) United States Patent
Florea

(10) Patent No.: US 7,074,212 B1
(45) Date of Patent: Jul. 11, 2006

(54) FLOW REGULATOR DEVICE AND METHOD OF USING

(76) Inventor: Erica J. Florea, 5308 NW. 84 Way, Coral Springs, FL (US) 33067

( * ) Notice: Subject to any disclaimer, the term of this patent is extended or adjusted under 35 U.S.C. 154(b) by 671 days.

(21) Appl. No.: 10/317,725

(22) Filed: Dec. 11, 2002

(51) Int. Cl.
*A61M 5/00* (2006.01)

(52) U.S. Cl. ........................................ 604/246; 604/250
(58) Field of Classification Search ................ 604/246, 604/250, 257, 259, 260; 137/825
See application file for complete search history.

(56) References Cited

U.S. PATENT DOCUMENTS

| | | | | |
|---|---|---|---|---|
| 4,425,116 A | * | 1/1984 | Bilstad et al. | 604/34 |
| 4,559,036 A | * | 12/1985 | Wunsch | 604/81 |
| 4,795,441 A | * | 1/1989 | Bhatt | 604/124 |
| 5,643,217 A | * | 7/1997 | Dobkin | 604/180 |
| 5,649,905 A | * | 7/1997 | Zanger et al. | 604/34 |
| 5,891,107 A | * | 4/1999 | Carr | 604/259 |

\* cited by examiner

*Primary Examiner*—LoAn H. Thanh (57) ABSTRACT

A flow regulator device and an associated method of using the device to constrict the flow of fluid through an intravenous line is disclosed. The device comprises a first component pivotally attached to a second component by a hinge. The first and second components are coupleable together into a closed book-like position for enshrouding an intravenous transfer line within a cylindrical tubing channel traversing along the device. A semi-elliptical pinch-off wheel is attached to the device so that the enshrouded transfer line may be progressively pinched off by the semi-elliptical pinch-off wheel in order to variably restrict the flow of liquid through the transfer line. A crossbar having an indicating end is attached to the wheel for indicating the flow rate through the enshrouded and constricted transfer line. The method of using comprises the steps of adjusting, attaching, hanging, injecting, noting, obtaining, placing, pushing, recording, rotating, securing, sterilizing, turning, and twisting.

11 Claims, 3 Drawing Sheets

FLOW REGULATOR DEVICE AND METHOD OF USING

FIELD OF THE INVENTION

The present invention relates to a flow control process and apparatus for fluid delivery systems in which fluid is dispensed from a fluid reservoir or container under the control of a pump. More particularly, the invention relates to controlling the rate of delivery of fluid administered to a patient by an intravenous infusion system utilizing a standard administration set.

DESCRIPTION OF THE PRIOR ART

Many applications in the field of intravenous infusion therapy require precise control of the accuracy in administering both the total volume to be infused and the rate at which infusion takes place. Such precise infusions are usually undertaken with the aid of devices commonly referred to as "volumetric infusion pumps" wherein accurate delivery is achieved by means of precisely made sections of tubing or cylinders which contain a known volume of fluid and from which this fluid is discharged at a known rate, thereby accurately dispensing specific volumes of fluid at preset delivery rates.

Whilst satisfactory in operation, the main disadvantage of such infusion pumps is the need for special tubes or cylinders, which, once used, must be discarded for reasons of sterility. Compared, therefore, with a conventional gravity infusion apparatus, which employs a cheap standard administration set, the cost per infusion using a volumetric infusion pump is relatively expensive. Furthermore, the disposables inventory at a medical establishment must be increased to include special items required by these volumetric pumps.

Normal gravity infusion, although low in cost owing to the use of mass-produced disposable standard administration sets, is totally unsuitable for precisely controlled infusions because the accuracy of delivery cannot be practically controlled even with the aid of a conventional flow controller. Similarly, the "drip-rate" type of device, over which control is maintained by counting drops, is capable of providing an accurate drop delivery rate, often with standard administration sets, but cannot provide volumetric accuracy owing to the wide variation in drop sizes.

For medical purposes, it is unacceptable to monitor flow-rate by means of a metering device introduced into a fluid stream being intravenously administered because this violates the required sterile barrier. Measurement must therefore be external to this barrier. Equally, measurement by passing fluid into a graduated container is unacceptably cumbersome and, without the addition of expensive equipment, precludes automatic calibration.

One type of pump that does not violate the required sterile barrier is a peristaltic pump. The latter can be arranged to deliver fluid using a standard administration set and may be provided with controls that regulate the speed of the motor and, hence, the pumping rate during operation of the pump. Adjustment of the controls to vary the speed of the motor changes the rate of fluid delivery and the pump may incorporate a visual display to indicate to the operator the rate of fluid flow for a selected position of the controls. The pump may also include a facility for adjusting the display to conform to the actual pumping performance of the tube on which it is operating by measurement of a known volume in a known time. This synchronising of actual performance with displayed performance is known as calibration.

Once calibrated, it would be reasonable to expect the actual delivery rate, over the speed range of the motor, when operating on other administration sets of the same type to comply with that selected by the controls and indicated by the display and, within certain limits, this is normally the case. However, variations in the delivery performance of tubing of the type used on standard administration sets are such that repeatability of calibrated performance on different samples of the same tube and in different environments is insufficient to maintain volumetric accuracy of the delivery for precise infusion applications, as referred to above. Moreover, the performance of tubing used in administration sets supplied from different sources can vary markedly. There are many reasons why the performance of tubing varies when used for pumping applications, but there is no need to expand on these in the present specification. Suffice it to say that unacceptable variations occur and these have hitherto precluded the use of peristaltic pumps for infusions requiring precise volumetric delivery, even when calibrated for the type of tube in actual use.

Variations in tubing performance can largely be eliminated if calibration is carried out directly on the tubing to be used for each infusion since, in this way, both actual and selected fluid delivery can be synchronized with accuracy at the outset of the infusion. However, this approach is tedious and time consuming and is still subject to error because the delivery capacity of the tubing can alter during infusion for various mechanical and environmental reasons.

Having regard to the foregoing, it will be apparent that apparatus in which accurate volumetric delivery can be achieved with standard administration sets would be of considerable advantage in reducing the cost per infusion and alleviating the need for high-cost special disposable items in the inventory of medical establishments.

A wide variety of flow regulator devices is currently available on the commercial market and an even larger number of these types of devices are known in the art of flow regulator devices, for example, the fluid flow control process and apparatus disclosed by Wheeldon et al. in U.S. Pat. No. 4,670,007; the apparatus for controlling the flow of an infusion fluid in an infusion system disclosed by Gijselhart et al. in U.S. Pat. No. 4,909,786; the IV clamp with tube clip disclosed by Archibald in U.S. Pat. No. 5,154,704; the in-line fluid monitor system and method disclosed by Goldberg et al. in U.S. Pat. No. 5,260,665; and the device for monitoring an dcontrolling an intravenous infusion system disclosed by Bellifemine in U.S. Pat. No. 5,439,442.

While all of the above-described devices fulfill their respective, particular objectives and requirements, the aforementioned patents do not describe a flow regulator device having a first component pivotally attached to a second component by a hinge wherein the first and second components are coupleable together into a closed book-like position. This combination of elements would specifically match the user's particular individual needs of making it possible to enshroud an intravenous transfer line within a cylindrical tubing channel traversing longitudinally along the device so that a semi-elliptical pinch-off wheel may be used to progressively pinch off the enshrouded transfer line to variably restrict the flow of liquid through the transfer line.

The above-described patents make no provision for a flow regulator device having a first component pivotally attached to a second component by a hinge wherein the first and second components are coupleable together into a closed book-like position.

Therefore, a need exists for a new and improved flow regulator device having a first component pivotally attached to a second component by a hinge wherein the first and second components are coupleable together into a closed book-like position. In this respect, the flow regulator device according to the present invention substantially departs from the conventional concepts and designs of the prior art, and in doing so provides an apparatus primarily developed for the purpose of providing a means for enshrouding an intravenous transfer line within a cylindrical tubing channel traversing longitudinally along the device so that means for progressively pinching off the enshrouded transfer line may be realized to variably restrict the flow of liquid through the transfer line.

SUMMARY OF THE INVENTION

The present device and associated method of using, according to the principles of the present invention, overcomes the shortcomings of the prior art by providing a flow regulator device and method of using is disclosed in which the device comprises a first component pivotally attached to a second component by a hinge. The first and second components are coupleable together into a closed book-like position for enshrouding an intravenous transfer line within a cylindrical tubing channel traversing along the device. A semi-elliptical pinch-off wheel is attached to the device so that the enshrouded transfer line may be progressively pinched off by the semi-elliptical pinch-off wheel in order to variably restrict the flow of liquid through the transfer line. A crossbar having an indicating end is attached to the wheel for indicating the flow rate through the enshrouded and constricted transfer line. The method of using comprises the steps of adjusting, attaching, hanging, injecting, noting, obtaining, placing, pushing, recording, rotating, securing, sterilizing, turning, and twisting.

In view of the foregoing disadvantages inherent in the known type flow regulator devices now present in the prior art, the present invention provides an improved flow regulator device, which will be described subsequently in great detail, is to provide a new and improved flow regulator device which is not anticipated, rendered obvious, suggested, or even implied by the prior art, either alone or in any combination thereof.

To attain this, the present invention essentially comprises a first component pivotally attached to a second component by a hinge. The first and second components are coupleable together into a closed book-like position for enshrouding an intravenous transfer line within a cylindrical tubing channel traversing along the device. A semi-elliptical pinch-off wheel is attached to the device so that the enshrouded transfer line may be progressively pinched off by the semi-elliptical pinch-off wheel in order to variably restrict the flow of liquid through the transfer line. A crossbar having an indicating end is attached to the wheel for indicating the flow rate through the enshrouded and constricted transfer line.

There has thus been outlined, rather broadly, the more important features of the invention in order that the detailed description thereof that follows may be better understood, and in order that the present contribution of the art may be better appreciated.

Numerous objects, features and advantages of the present invention will be readily apparent to those of ordinary skill in the art upon reading of the following detailed description of presently preferred, but nonetheless illustrative, embodiments of the present invention when taken in conjunction with the accompany drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved flow regulator device that has all the advantages of the prior art flow regulator device and none of the disadvantages.

It is another object of the present invention to provide a new and improved flow regulator device that may be easily and efficiently manufactured and marketed.

An even further object of the present invention is to provide a new and improved flow regulator device that has a low cost of manufacture with regard to both materials and labor, and which accordingly is then susceptible of low prices of sale to the consuming public, thereby making such multipurpose storage unit and system economically available to the buying public.

Still another object of the present invention is to provide a new flow regulator device that provides in the apparatuses and methods of the prior art some of the advantages thererof, while simultaneously overcoming some of the disadvantages normally associated therewith.

Even still another object of the present invention is to provide a flow regulator device having a first component pivotally attached to a second component by a hinge wherein the first and second components are coupleable together into a closed book-like position. This combination of elements makes it possible to enshroud an intravenous transfer line within a cylindrical tubing channel traversing longitudinally along the device so that a semi-elliptical pinch-off wheel may be used to progressively pinch off the enshrouded transfer line to variably restrict the flow of liquid through the transfer line.

Lastly, it is an object of the present invention to provide a new and improved method of using comprising the steps of adjusting, attaching, hanging, injecting, noting, obtaining, placing, pushing, recording, rotating, securing, sterilizing, turning, and twisting.

Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and description matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various figures.

DETAILED DESCRIPTION OF THE PREFERRED EMBODIMENT

Referring now to the drawings, and in particular FIGS. 1 to 4 thereof, one preferred embodiment of the present invention is shown and generally designated by the reference numeral 10. One preferred embodiment of a flow regulator device 10 for controlling the flow rate of a fluid through an intravenous transfer line 12, the device 10 comprises a first component 14, a hinge 18, and a second component 20. The first component 14 has a back, a front, an exterior side, an interior side, a top and a bottom, the first component 14 includes a first concave ridge, a first top protrusion, and a first bottom protrusion. The first concave ridge traverses longitudinally through the rear portion of the interior side of the first component 14, in which the first concave ridge defines a first concave groove 16. The first top protrusion is attached to the front top portion of the interior side of the first component 14. The first bottom protrusion is attached to the front bottom portion of the interior side of the first component 14, wherein a portion of the interior side of the first component 14, the first top protrusion and the first bottom protrusion define a first cavity having a truncated elliptical shape. The hinge 18 is attached to the back of the first component 14. The second component 20 has a back, a front, an exterior side, an interior side, a top and a bottom. The back of the second component 20 is attached to the hinge 18, wherein the first component 14 and the second component 20 pivotally hinged together. When the first component 14 is pivoted towards the second component 20 then the device 10 is in a closed position. When the first component 14 is pivoted away from the second component 20 then the device 10 is in an open position. The second component 20 includes a second concave ridge, a second top protrusion, a second bottom protrusion, a hollow chamber 24, a plurality of holes 26, a semi-elliptical pinch-off wheel 28, a crossbar 32, and a plurality of volumetric markings 36. The second concave ridge traverses longitudinally through the rear portion of the interior side of the second component 20, wherein the second concave ridge defining a second concave groove 22. When the device 10 is in the closed position, then the first concave ridge and the second concave ridge defines a substantially hollow cylindrical tubing channel traversing longitudinally through the device 10. The second top protrusion is attached to the front top portion of the interior side of the second component 20. The second bottom protrusion, the second top protrusion and the second bottom protrusion define a second cavity having a truncated elliptical shape. The second bottom protrusion is attached to the front bottom portion of the interior side of the second component 20, wherein a portion of the interior side of the second component 20, the second top protrusion and the second bottom protrusion define a second cavity having a truncated elliptical shape. When the device 10 is in a closed position then the first cavity of the first component 14 and the second cavity of the second component 20 define a truncated elliptical chamber. The hollow chamber 24 is defined by the top, bottom, front, back, exterior side and interior side of the second component 20. The plurality of holes 26 traverses through the front of the second component 20 into the hollow chamber 24 of the second component 20. The semi-elliptical pinch-off wheel 28 having an axle 30, in which the axle 30 of the semi-elliptical pinch-off wheel 28 is rotatably attached to the interior side of the second component 20. The axle 30 traverses through the interior side of the second component 20 into the hollow chamber 24 of the second component 20. When the device 10 is in the closed position then a first portion of the circumference of the semi-elliptical pinch-off wheel 28 extending within the hollow cylindrical tubing channel of the device 10 and a second portion of the circumference of the semi-elliptical pinch-off wheel 28 does not extend within the hollow cylindrical tubing channel of the device 10. The crossbar 32 has an indicating end 34, in which the crossbar 32 is attached substantially perpendicularly to the axle 30 of the semi-elliptical pinch-off wheel 28. The crossbar 32 positioned within the hollow chamber 24 of the second component 20 with the indicating end 34 positionable at any hole 26 of the plurality of holes 26. The plurality of volumetric markings 36 is embossed on the front of the second component 20, in which each volumetric marking of the plurality of volumetric markings 36 is aligned to correspond to a separate corresponding hole 26 of the plurality of holes 26 traversing through the front of the second component 20.

Another preferred embodiment the flow regulator device 10 consists essentially of: a first component 14, a hinge 18, and a second component 20. The first component 14 has a back, a front, an exterior side, an interior side, a top and a bottom, the first component 14 includes a first concave ridge, a first top protrusion, and a first bottom protrusion. The first concave ridge traverses longitudinally through the rear portion of the interior side of the first component 14, in which the first concave ridge defines a first concave groove 16. The first top protrusion is attached to the front top portion of the interior side of the first component 14. The first bottom protrusion is attached to the front bottom portion of the interior side of the first component 14, wherein a portion of the interior side of the first component 14, the first top protrusion and the first bottom protrusion define a first cavity having a truncated elliptical shape. The hinge 18 is attached to the back of the first component 14. The second component 20 has a back, a front, an exterior side, an interior side, a top and a bottom. The back of the second component 20 is attached to the hinge 18, wherein the first component 14 and the second component 20 pivotally hinged together. When the first component 14 is pivoted towards the second component 20 then the device 10 is in a closed position.

When the first component 14 is pivoted away from the second component 20 then the device 10 is in an open position. The second component 20 includes a second concave ridge, a second top protrusion, a second bottom protrusion, a hollow chamber 24, a plurality of holes 26, a semi-elliptical pinch-off wheel 28, a crossbar 32, and a plurality of volumetric markings 36. The second concave ridge traverses longitudinally through the rear portion of the interior side of the second component 20, wherein the second concave ridge defining a second concave groove 22. When the device 10 is in the closed position, then the first concave ridge and the second concave ridge defines a substantially hollow cylindrical tubing channel traversing longitudinally through the device 10. The second top protrusion is attached to the front top portion of the interior side of the second component 20. The second bottom protrusion, the second top protrusion and the second bottom protrusion define a second cavity having a truncated elliptical shape. The second bottom protrusion is attached to the front bottom portion of the interior side of the second component 20, wherein a portion of the interior side of the second component 20, the second top protrusion and the second bottom protrusion define a second cavity having a truncated elliptical shape. When the device 10 is in a closed position then the first cavity of the first component 14 and the second cavity of the second component 20 define a truncated elliptical chamber. The hollow chamber 24 is defined by the top, bottom, front, back, exterior side and interior side of the second component 20. The plurality of holes 26 traverses through the front of the second component 20 into the hollow chamber 24 of the second component 20. The semi-elliptical pinch-off wheel 28 having an axle 30, in which the axle 30 of the semi-elliptical pinch-off wheel 28 is rotatably attached to the interior side of the second component 20. The axle 30 traverses through the interior side of the second component 20 into the hollow chamber 24 of the second component 20. When the device 10 is in the closed position then a first portion of the circumference of the semi-elliptical pinch-off wheel 28 extending within the hollow cylindrical tubing channel of the device 10 and a second portion of the circumference of the semi-elliptical pinch-off wheel 28 does not extend within the hollow cylindrical tubing channel of the device 10. The crossbar 32 has an indicating end 34, in which the crossbar 32 is attached substantially perpendicularly to the axle 30 of the semi-elliptical pinch-off wheel 28. The crossbar 32 positioned within the hollow chamber 24 of the second component 20 with the indicating end 34 positionable at any hole 26 of the plurality of holes 26. The plurality of volumetric markings 36 is embossed on the front of the second component 20, in which each volumetric marking of the plurality of volumetric markings 36 is aligned to correspond to a separate corresponding hole 26 of the plurality of holes 26 traversing through the front of the second component 20.

The device 10 may be made of any type of material. One preferred configuration of the device 10 is that the device 10 is made of a plastic selected from the group consisting of nylon, polyester, polypropylene, polyurethanes, polyacryls, polymethacryls, cellulosic polymers, styrene-acryl copolymers, polystyrene-polyacryl mixtures, polysiloxanes, polyesters, urethane-acryl copolymers, siloxane-urethane copolymers, polyurethane-polymethacryl mixtures, silicone-acryl copolymers, vinyl acetate polymers, and mixtures thereof. Another preferred configuration is that the device is that the device 10 is made of metal is selected from the group consisting of aluminum, scandium, titanium, vanadium, chromium, manganese, iron, cobalt, nickel, copper, zinc, molybdenum, ruthenium, rhodium, palladium, tungsten, and mixtures thereof.

One preferred embodiment of a method of using a flow regulator device 10 for controlling the flow rate of a fluid through an intravenous transfer line 12, the method comprising the steps of adjusting, attaching, hanging, injecting, noting, obtaining, placing, pushing, recording, rotating, securing, sterilizing, turning, and twisting. The obtaining step comprises obtaining the device 10 consisting essentially of: a first component 14 having a back, a front, an exterior side, an interior side, a top and a bottom, the first component 14 including: a first concave ridge traversing longitudinally through the rear portion of the interior side of the first component 14, wherein the first concave ridge defining a first concave groove 16; a first top protrusion attached to the front top portion of the interior side of the first component 14; and a first bottom protrusion attached to the front bottom portion of the interior side of the first component 14, wherein a portion of the interior side of the first component 14, the first top protrusion and the first bottom protrusion defining a first cavity having a truncated elliptical shape; a hinge 18 attached to the back of the first component 14; a second component 20 having a back, a front, an exterior side, an interior side, a top and a bottom, the back of the second component 20 attached to the hinge 18, wherein the first component 14 and the second component 20 pivotally hinge 18d together, so that when the first component 14 is pivoted towards the second component 20 then the device 10 is in a closed position, and so that when the first component 14 is pivoted away from the second component 20 then the device 10 is in an open position, the second component 20 including: a second concave ridge traversing longitudinally through the rear portion of the interior side of the second component 20, wherein the second concave ridge defining a second concave groove 22, wherein when the device 10 is in the closed position then the first concave ridge and the second concave ridge defining a substantially hollow cylindrical tubing channel traversing longitudinally through the device 10; a second top protrusion attached to the front top portion of the interior side of the second component 20; a second bottom protrusion, the second top protrusion and the second bottom protrusion defining a second cavity having a truncated elliptical shape; a second bottom protrusion attached to the front bottom portion of the interior side of the second component 20, wherein a portion of the interior side of the second component 20, the second top protrusion and the second bottom protrusion defining a second cavity having a truncated elliptical shape, wherein when the device 10 in a closed position then the first cavity of the first component 14 and the second cavity of the second component 20 defining a truncated elliptical chamber; a hollow chamber 24 defined by the top, bottom, front, back, exterior side and interior side of the second component 20; a plurality of holes 26 traversing through the front of the second component 20 into the hollow chamber 24 of the second component 20; a semi-elliptical pinch-off wheel 28 having an axle 30, the axle 30 of the semi-elliptical pinch-off wheel 28 rotatably attached to the interior side of the second component 20, wherein the axle 30 traversing through the interior side of the second component 20 into the hollow chamber 24 of the second component 20, wherein when the device 10 is in the closed position then a first portion of the circumference of the semi-elliptical pinch-off wheel 28 extending within the hollow cylindrical tubing channel of the device 10 and a second portion of the circumference of the semi-elliptical pinch-off wheel 28 not extending within the hollow cylindrical tubing channel of the device 10; a crossbar 32 having an indicating end 34, the crossbar 32 attached substantially perpendicularly to the axle 30 of the semi-elliptical pinch-off wheel 28, the crossbar 32 positioned within the hollow chamber 24 of the second component 20 with the indicating end 34 positionable at any hole 26 of the plurality of holes 26; and a plurality of volumetric markings 36 embossed on the front of the second component 20, each volumetric marking of the plurality of volumetric markings 36 aligned to correspond to a separate corresponding hole 26 of the plurality of holes 26 traversing through the front of the second component 20. The hanging step comprises hanging an intravenous bottle above a patient, the intravenous bottle having fluid contents and having the intravenous transfer line 12 fluidly connected to the bottle. The attaching step comprises attaching an intravenous needle to the transfer line 12 of the intravenous bottle so that the contents of the intravenous bottle are in fluid communications with the intravenous needle. The sterilizing step comprises sterilizing a portion of a designated injection zone on the patient. The injecting step comprises injecting the intravenous needle into the designated injection zone of the patient. The securing step comprises securing a portion of the injected intravenous needle onto the designated injection zone of the patient with adhesive tape. The twisting step comprises twisting rotatably the semi-elliptical pinch-off wheel 28 so that the second portion of the circumference of the semi-elliptical pinch-off wheel 28 does not extend within the hollow cylindrical tubing channel of the device 10. The turning step comprises turning pivotally away the first component 14 and the second component 20 so that the device 10 is positioned in the open position. The placing step comprises placing longitudinally a portion of the transfer line 12 into the second concave groove 22 of the second component 20 of the device 10 when the device 10 is in the open position. The pushing step comprises pushing pivotally together the first component 14 and the second component 20 so that the device 10 is positioned in the closed position while the portion of the transfer line 12 is placed in the second concave groove 22 of the device 10, so that the portion of the transfer line 12 is enshrouded by the hollow cylindrical tubing channel traversing longitudinally through the device 10. The rotating step comprises rotating the semi-elliptical pinch-off wheel 28 when the device 10 is positioned in the closed position while the portion of the transfer line 12 is placed in the second concave groove 22 of the device 10 so that the first portion of the circumference of the semi-elliptical pinch-off wheel 28 extends within the hollow cylindrical tubing channel of the device 10 wherein partially restricting the flow of fluid through the transfer line 12. The adjusting step comprises adjusting the position of the semi-elliptical pinch-off wheel 28 when the device 10 is positioned in the closed position while the portion of the transfer line 12 is placed in the second concave groove 22 of the device 10 by moving rotatably the semi-elliptical pinch-off wheel 28 while looking at the indicating end 34 of the crossbar 32 through the plurality of holes 26 in the front of the second component 20. The noting step comprises noting an estimated volumetric delivery rate from the plurality of volumetric markings 36 embossed on the front of the second component 20 corresponding to where the indicating end 34 of the crossbar 32 is seen through one of the plurality of holes 26. The recording step comprises recording the estimated volumetric delivery rate.

Figure 1:
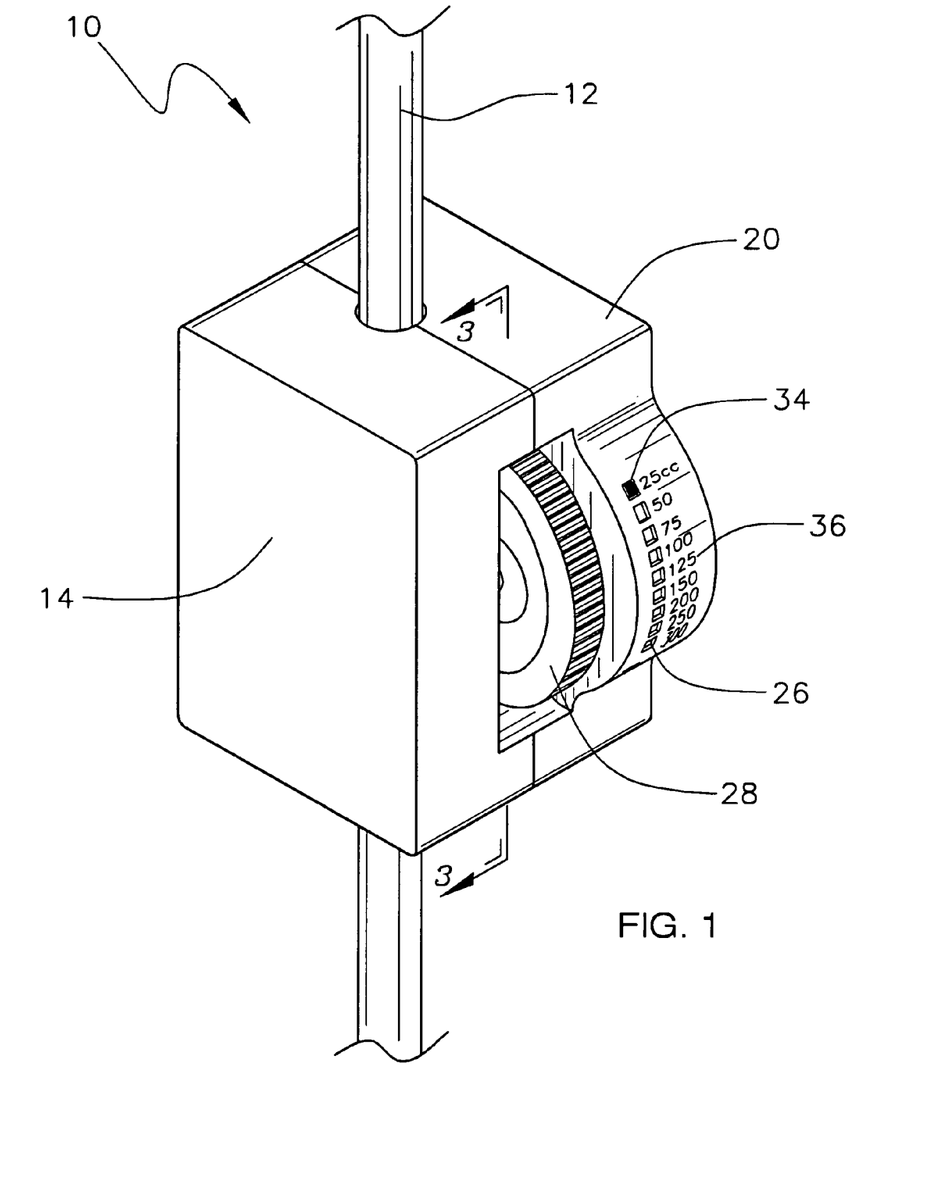
FIG. 1 is a perspective view of a preferred embodiment of the flow regulator device in accordance with the principles of the present invention.

Referring now to FIG. 1 which depicts a perspective view of an preferred embodiment of the flow regulator device 10 showing the device 10 in the closed position with a portion of the transfer line 12 enshrouded within the hollow cylindrical tubing channel traversing longitudinally through said device 10.

Figure 2:
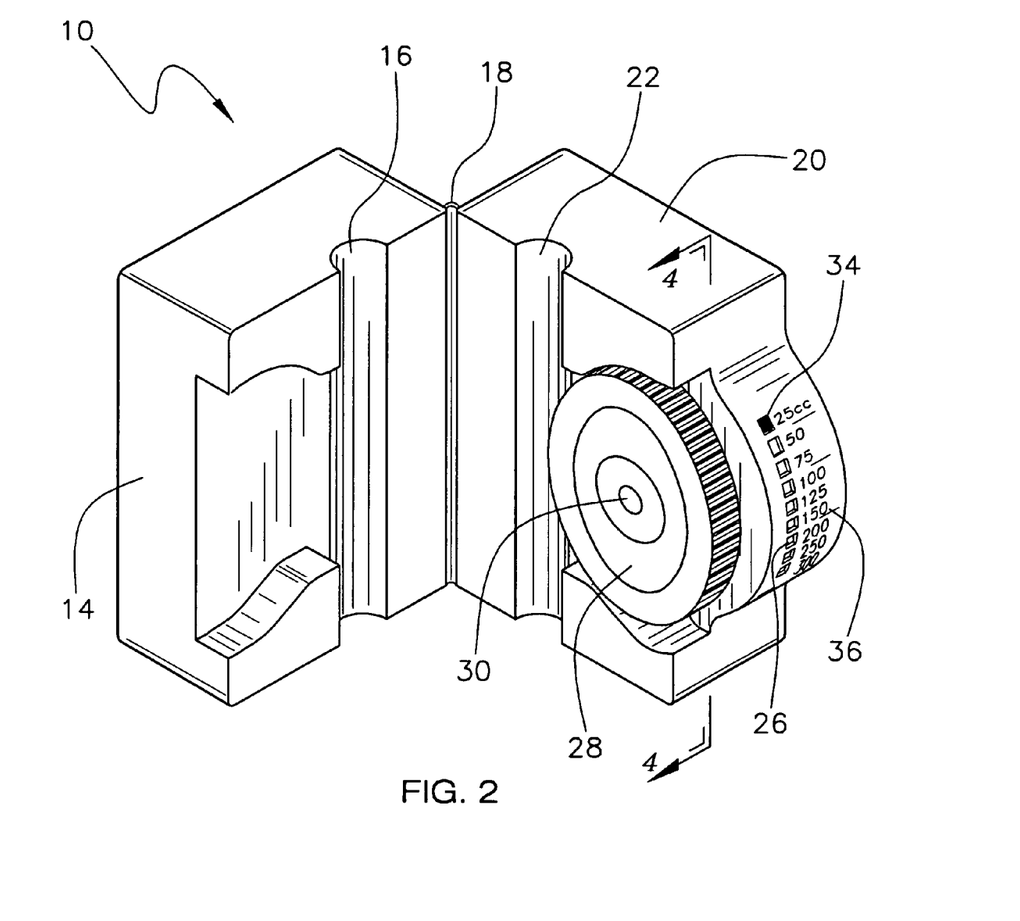
FIG. 2 is a perspective view of a preferred embodiment of the flow regulator device of the present invention.

Referring now to FIG. 2, which depicts a perspective view of a preferred embodiment of the flow regulator device 10 showing the device 10 in the open position.

Figure 3:
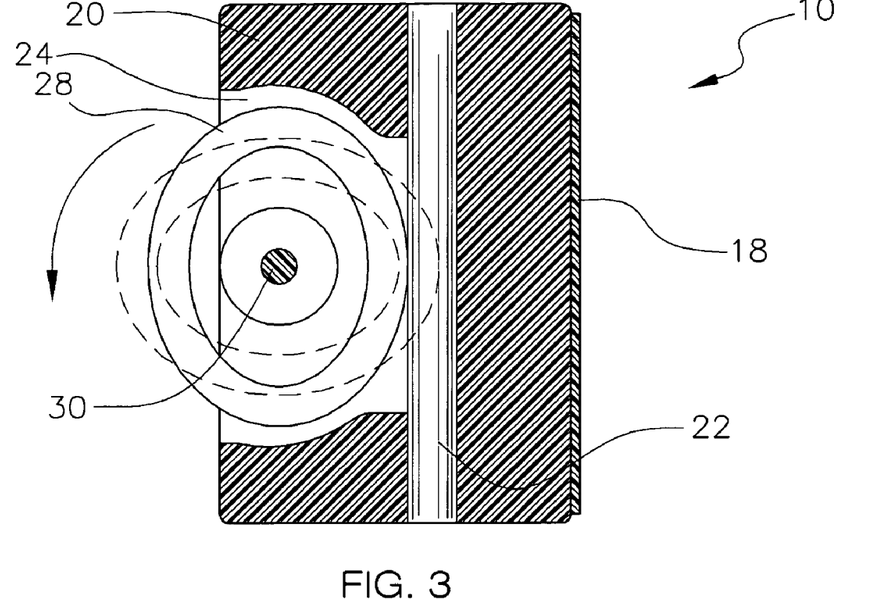
FIG. 3 is a cross sectional side view of a preferred embodiment of the flow regulator device of the present invention.
Figure 4:
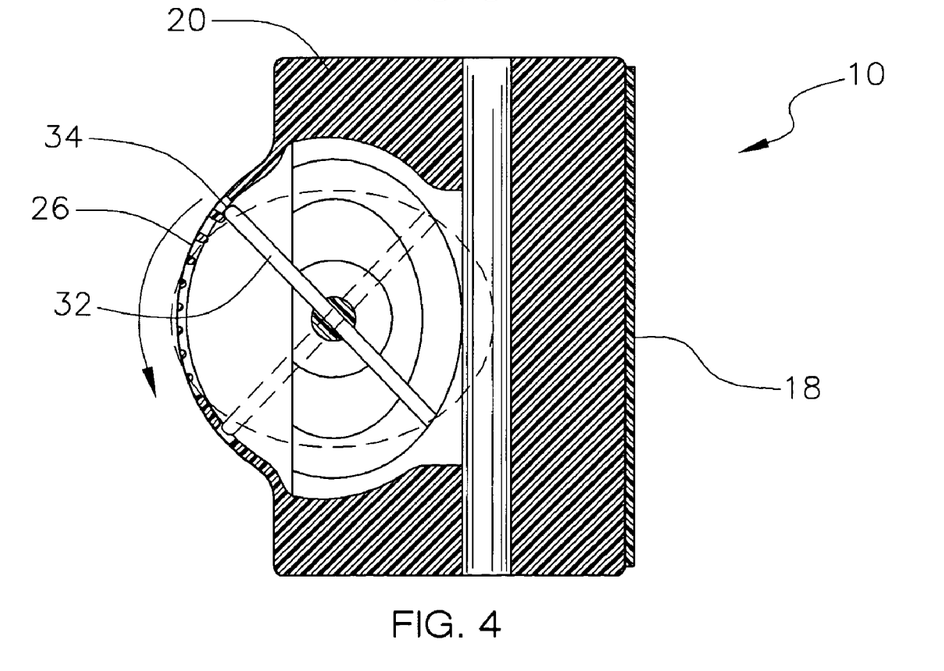
FIG. 4 is a cross sectional side view of a preferred embodiment of the flow regulator device of the present invention.

Referring now to FIG. 3 and FIG. 4 which depict a cross sectional side views of a preferred embodiment of the flow regulator device 10 showing the semi-elliptical pinch-off wheel 28 rotatably attached to the second component about the axle 30 rotatably attached to the interior side of the second component 20. Also shown is the crossbar 32 having the indicating end 34, in which the crossbar 32 is attached substantially perpendicularly to the axle 30 of the semi-elliptical pinch-off wheel 28. The crossbar 32 positioned within the hollow chamber 24 of the second component 20 with the indicating end 34 positionable at any hole 26 of the plurality of holes 26.

As to the manner of usage and operation of the present invention, the same should be apparent from the above description. Accordingly, no further discussion relating to the manner of usage and operation will be provided.

While a preferred embodiment of the flow regulator device has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Throughout this specification, unless the context requires otherwise, the word "comprise" or variations such as "comprises" or "comprising" or the term "includes" or variations, thereof, or the term "having" or variations, thereof will be understood to imply the inclusion of a stated element or integer or group of elements or integers but not the exclusion of any other element or integer or group of elements or integers. In this regard, in construing the claim scope, an embodiment where one or more features is added to any of the claims is to be regarded as within the scope of the invention given that the essential features of the invention as claimed are included in such an embodiment.

Those skilled in the art will appreciate that the invention described herein is susceptible to variations and modifications other than those specifically described. It is to be understood that the invention includes all such variations and modifications that fall within its spirit and scope. The invention also includes all of the steps, features, compositions and compounds referred to or indicated in this specification, individually or collectively, and any and all combinations of any two or more of said steps or features.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A flow regulator device for controlling the flow rate of a fluid through an intravenous transfer line, said device comprising:

a first component having a back, a front, an exterior side, an interior side, a top and a bottom, said first component including:
  a first concave ridge traversing longitudinally through the rear portion of the interior side of said first component, wherein said first concave ridge defining a first concave groove;
  a first top protrusion attached to the front top portion of the interior side of said first component; and
  a first bottom protrusion attached to the front bottom portion of the interior side of said first component, wherein a portion of said interior side of said first component, said first top protrusion and said first bottom protrusion defining a first cavity having a truncated elliptical shape;
a hinge attached to the back of said first component; and
a second component having a back, a front, an exterior side, an interior side, a top and a bottom, the back of said second component attached to said hinge, wherein said first component and said second component pivotally hinged together, so that when said first component is pivoted towards said second component then said device is in a closed position, and so that when said first component is pivoted away from said second component then said device is in an open position, said second component including:
  a second concave ridge traversing longitudinally through the rear portion of the interior side of said second component, wherein said second concave ridge defining a second concave groove, wherein when said device is in the closed position then said first concave ridge and said second concave ridge defining a substantially hollow cylindrical tubing channel traversing longitudinally through said device;
  a second top protrusion attached to the front top portion of the interior side of said second component;
  a second bottom protrusion, said second top protrusion and said second bottom protrusion defining a second cavity having a truncated elliptical shape;
  a second bottom protrusion attached to the front bottom portion of the interior side of said second component, wherein a portion of said interior side of said second component, said second top protrusion and said second bottom protrusion defining a second cavity having a truncated elliptical shape, wherein when the device in a closed position then the first cavity of said first component and the second cavity of said second component defining a truncated elliptical chamber;
  a hollow chamber defined by the top, bottom, front, back, exterior side and interior side of said second component;
  a plurality of holes traversing through the front of said second component into the hollow chamber of said second component;
  a semi-elliptical pinch-off wheel having an axle, said axle of said semi-elliptical pinch-off wheel rotatably attached to the interior side of said second component, wherein said axle traversing through the interior side of said second component into the hollow chamber of said second component, wherein when said device is in the closed position then a first portion of the circumference of said semi-elliptical pinch-off wheel extending within the hollow cylindrical tubing channel of said device and a second portion of the circumference of said semi-elliptical pinch-off wheel not extending within the hollow cylindrical tubing channel of said device;
  a crossbar having an indicating end, said crossbar attached substantially perpendicularly to said axle of said semi-elliptical pinch-off wheel, said crossbar positioned within the hollow chamber of said second component with said indicating end positionable at any hole of said plurality of holes; and
  a plurality of volumetric markings embossed on the front of said second component, each volumetric marking of said plurality of volumetric markings aligned to correspond to a separate corresponding hole of said plurality of holes traversing through the front of said second component.

2. The device of claim 1 wherein the device is made of a plastic.

3. The device of claim 2 wherein said plastic is selected from the group consisting of nylon, polyester, polypropylene, polyurethanes, polyacryls, polymethacryls, cellulosic polymers, styrene-acryl copolymers, polystyrene-polyacryl mixtures, polysiloxanes, polyesters, urethane-acryl copolymers, siloxane-urethane copolymers, polyurethane-polymethacryl mixtures, silicone-acryl copolymers, vinyl acetate polymers, and mixtures thereof.

4. The device of claim 1 wherein the device is made of metal.

5. The device of claim 4 wherein said metal is selected from the group consisting of aluminum, scandium, titanium, vanadium, chromium, manganese, iron, cobalt, nickel, copper, zinc, molybdenum, ruthenium, rhodium, palladium, tungsten, and mixtures thereof.

6. A flow regulator device for controlling the flow rate of a fluid through an intravenous transfer line, said device consisting essentially of:
  a first component having a back, a front, an exterior side, an interior side, a top and a bottom, said first component including:
    a first concave ridge traversing longitudinally through the rear portion of the interior side of said first component, wherein said first concave ridge defining a first concave groove;
    a first top protrusion attached to the front top portion of the interior side of said first component; and
    a first bottom protrusion attached to the front bottom portion of the interior side of said first component, wherein a portion of said interior side of said first component, said first top protrusion and said first bottom protrusion defining a first cavity having a truncated elliptical shape;
  a hinge attached to the back of said first component; and
  a second component having a back, a front, an exterior side, an interior side, a top and a bottom, the back of said second component attached to said hinge, wherein said first component and said second component pivotally hinged together, so that when said first component is pivoted towards said second component then said device is in a closed position, and so that when said first component is pivoted away from said second component then said device is in an open position, said second component including:
    a second concave ridge traversing longitudinally through the rear portion of the interior side of said second component, wherein said second concave ridge defining a second concave groove, wherein when said device is in the closed position then said first concave ridge and said second concave ridge defining a substantially hollow cylindrical tubing channel traversing longitudinally through said device;

a second top protrusion attached to the front top portion of the interior side of said second component;

a second bottom protrusion, said second top protrusion and said second bottom protrusion defining a second cavity having a truncated elliptical shape;

a second bottom protrusion attached to the front bottom portion of the interior side of said second component, wherein a portion of said interior side of said second component, said second top protrusion and said second bottom protrusion defining a second cavity having a truncated elliptical shape, wherein when the device in a closed position then the first cavity of said first component and the second cavity of said second component defining a truncated elliptical chamber;

a hollow chamber defined by the top, bottom, front, back, exterior side and interior side of said second component;

a plurality of holes traversing through the front of said second component into the hollow chamber of said second component;

a semi-elliptical pinch-off wheel having an axle, said axle of said semi-elliptical pinch-off wheel rotatably attached to the interior side of said second component, wherein said axle traversing through the interior side of said second component into the hollow chamber of said second component, wherein when said device is in the closed position then a first portion of the circumference of said semi-elliptical pinch-off wheel extending within the hollow cylindrical tubing channel of said device and a second portion of the circumference of said semi-elliptical pinch-off wheel not extending within the hollow cylindrical tubing channel of said device;

a crossbar having an indicating end, said crossbar attached substantially perpendicularly to said axle of said semi-elliptical pinch-off wheel, said crossbar positioned within the hollow chamber of said second component with said indicating end positionable at any hole of said plurality of holes; and a plurality of volumetric markings embossed on the front of said second component, each volumetric marking of said plurality of volumetric markings aligned to correspond to a separate corresponding hole of said plurality of holes traversing through the front of said second component.

7. The device of claim 6 wherein the device is made of a plastic.

8. The device of claim 7 wherein said plastic is selected from the group consisting of nylon, polyester, polypropylene, polyurethanes, polyacryls, polymethacryls, cellulosic polymers, styrene-acryl copolymers, polystyrene-polyacryl mixtures, polysiloxanes, polyesters, urethane-acryl copolymers, siloxane-urethane copolymers, polyurethane-polymethacryl mixtures, silicone-acryl copolymers, vinyl acetate polymers, and mixtures thereof.

9. The device of claim 6 wherein the device is made of metal.

10. The device of claim 9 wherein said metal is selected from the group consisting of aluminum, scandium, titanium, vanadium, chromium, manganese, iron, cobalt, nickel, copper, zinc, molybdenum, ruthenium, rhodium, palladium, tungsten, and mixtures thereof.

11. A method of using a flow regulator device for controlling the flow rate of a fluid through an intravenous transfer line, said method comprising:

obtaining the device consisting essentially of:
a first component having a back, a front, an exterior side, an interior side, a top and a bottom, the first component including:
a first concave ridge traversing longitudinally through the rear portion of the interior side of the first component, wherein the first concave ridge defining a first concave groove;
a first top protrusion attached to the front top portion of the interior side of the first component; and
a first bottom protrusion attached to the front bottom portion of the interior side of the first component, wherein a portion of the interior side of the first component, the first top protrusion and the first bottom protrusion defining a first cavity having a truncated elliptical shape;

a hinge attached to the back of the first component; and a second component having a back, a front, an exterior side, an interior side, a top and a bottom, the back of the second component attached to the hinge, wherein the first component and the second component pivotally hinged together, so that when the first component is pivoted towards the second component then the device is in a closed position, and so that when the first component is pivoted away from the second component then the device is in an open position, the second component including:
a second concave ridge traversing longitudinally through the rear portion of the interior side of the second component, wherein the second concave ridge defining a second concave groove, wherein when the device is in the closed position then the first concave ridge and the second concave ridge defining a substantially hollow cylindrical tubing channel traversing longitudinally through the device;
a second top protrusion attached to the front top portion of the interior side of the second component;
a second bottom protrusion, the second top protrusion and the second bottom protrusion defining a second cavity having a truncated elliptical shape;
a second bottom protrusion attached to the front bottom portion of the interior side of the second component, wherein a portion of the interior side of the second component, the second top protrusion and the second bottom protrusion defining a second cavity having a truncated elliptical shape, wherein when the device in a closed position then the first cavity of the first component and the second cavity of the second component defining a truncated elliptical chamber;
a hollow chamber defined by the top, bottom, front, back, exterior side and interior side of the second component;
a plurality of holes traversing through the front of the second component into the hollow chamber of the second component;
a semi-elliptical pinch-off wheel having an axle, the axle of the semi-elliptical pinch-off wheel rotatably attached to the interior side of the second component, wherein the axle traversing through the interior side of the second component into the hollow chamber of the second component, wherein when the device is in the closed position then a first portion of the circumference of the semi-elliptical pinch-off wheel extending within the hollow cylindrical tubing channel of the device and a second portion of the circumference of the semi-elliptical pinch-off wheel not extending within the hollow cylindrical tubing channel of the device;

a crossbar having an indicating end, the crossbar attached substantially perpendicularly to the axle of the semi-elliptical pinch-off wheel, the crossbar positioned within the hollow chamber of the second component with the indicating end positionable at any hole of the plurality of holes; and a plurality of volumetric markings embossed on the front of the second component, each volumetric marking of the plurality of volumetric markings aligned to correspond to a separate corresponding hole of the plurality of holes traversing through the front of the second component;

hanging an intravenous bottle above a patient, the intravenous bottle having fluid contents and having the intravenous transfer line fluidly connected to the bottle;

attaching an intravenous needle to the transfer line of the intravenous bottle so that the contents of the intravenous bottle are in fluid communications with the intravenous needle;

sterilizing a portion of a designated injection zone on the patient;

injecting the intravenous needle into the designated injection zone of the patient;

securing a portion of the injected intravenous needle onto the designated injection zone of the patient with adhesive tape;

twisting rotatably the semi-elliptical pinch-off wheel so that the second portion of the circumference of said semi-elliptical pinch-off wheel does not extend within the hollow cylindrical tubing channel of said device;

turning pivotally away the first component and the second component so that the device is positioned in the open position;

placing longitudinally a portion of the transfer line into the second concave groove of the second component of the device when the device is in the open position;

pushing pivotally together the first component and the second component so that the device is positioned in the closed position while the portion of the transfer line is placed in the second concave groove of the device, so that the portion of the transfer line is enshrouded by the hollow cylindrical tubing channel traversing longitudinally through said device;

rotating the semi-elliptical pinch-off wheel when the device is positioned in the closed position while the portion of the transfer line is placed in the second concave groove of the device so that the first portion of the circumference of said semi-elliptical pinch-off wheel extends within the hollow cylindrical tubing channel of said device wherein partially restricting the flow of fluid through the transfer line;

adjusting the position of the semi-elliptical pinch-off wheel when the device is positioned in the closed position while the portion of the transfer line is placed in the second concave groove of the device by moving rotatably the semi-elliptical pinch-off wheel while looking at the indicating end of the crossbar through the plurality of holes in the front of said second component;

noting an estimated volumetric delivery rate from the plurality of volumetric markings embossed on the front of said second component corresponding to where the indicating end of the crossbar is seen through one of the plurality of holes; and recording the estimated volumetric delivery rate.

* * * * *